United States Patent [19]
Cotrel

[11] Patent Number: 5,385,583
[45] Date of Patent: Jan. 31, 1995

[54] IMPLANT FOR AN OSTEOSYNTHESIS DEVICE, PARTICULAR FOR THE SPINE

[75] Inventor: Yves P. C. Cotrel, Paris, France

[73] Assignee: Sofamor, Paris, France

[21] Appl. No.: 126,071

[22] Filed: Sep. 23, 1993

Related U.S. Application Data

[63] Continuation of Ser. No. 851,946, Mar. 13, 1992, abandoned.

[30] Foreign Application Priority Data

Aug. 19, 1991 [FR] France ................................ 91-10402

[51] Int. Cl.⁶ ................................................ A61F 2/44
[52] U.S. Cl. ........................................ 623/17; 606/61; 606/73
[58] Field of Search ........................ 623/16, 17; 606/60, 606/61, 69, 72, 73

[56] References Cited

U.S. PATENT DOCUMENTS

| | | | |
|---|---|---|---|
| 5,019,078 | 5/1991 | Perren et al. | 606/61 |
| 5,076,955 | 11/1991 | Cotrel | 606/61 |

FOREIGN PATENT DOCUMENTS

| | | | |
|---|---|---|---|
| 0348272 | 12/1989 | European Pat. Off. | 623/17 |
| 2638632 | 5/1990 | France | 623/17 |

*Primary Examiner*—Randy C. Shay
*Attorney, Agent, or Firm*—Woodard, Emhardt, Naughton, Moriarty & McNett

[57] ABSTRACT

The implant comprises a part (2) for anchorage in the bone and a body (3) for fixing on a rod (4), the body comprising two lateral branches (5) defining a passageway (6) which is open on each side of the body for receiving the rod, and a screw-threaded plug (8) adapted to be screwed between the branches; a strip (14), interposed between the plug and the rod, is fixed to a ring (15) with which it constitutes a pellet (16). The strip (14) is curved and defines a concave surface (14a) adapted to be applied against the surface of the rod. The curvature of the strip (14) permits clamping the rod (4) in position with a relatively small clamping pressure in that the forces are distributed, which improves resistance to alternating bending of the rod in the body (3) and resistance to fatigue.

14 Claims, 1 Drawing Sheet

5,385,583

IMPLANT FOR AN OSTEOSYNTHESIS DEVICE, PARTICULAR FOR THE SPINE

This application is a continuation of application Ser. No. 07/851,946, filed Mar. 13, 1992, now abandoned.

The present invention relates to an implant for an osteosynthesis device, in particular for the backbone, comprising a part for anchorage in the bone and a body for fixing on a rod, wherein the body comprises two lateral branches defining therebetween a passageway opening onto a rear part of the body and open on each side of the body for receiving the rod, said implant further comprising a screwthreaded plug adapted to be screwed in tappings formed on the inner sides of the two lateral branches.

According to the invention, the implant comprises, between the plug and the rod, an element fixed to means for positioning it with respect to the branches of the body, said element being a curved strip defining adjacent to the rod a concave surface adapted to be applied against the surface of the rod.

Consequently, the area of the surface of the strip in contact with the rod is very large, which permits distributing the pressure of contact in an improved manner and therefore reducing said pressure and also increasing the bending inertia of the strip relative to a flat strip.

According to an embodiment, the concave surface of the strip is a portion of a cylinder whose radius of curvature substantially corresponds to the radius of curvature of the surface of the rod, the strip consequently having a substantially half-round tile shape.

According to another feature of the invention, the strip is cut substantially in the middle of the strip and is consequently formed by two semi-strips separated by a slot substantially perpendicular to the axis of the rod.

These two semi-strips result in an improved contact on a curved or inclined rod in the passageway of the screw.

Further features and advantages of the invention will be apparent from the following description with reference to the accompanying drawings which illustrate three embodiments of the invention as non-limitative examples.

In the drawings

Figure 1:
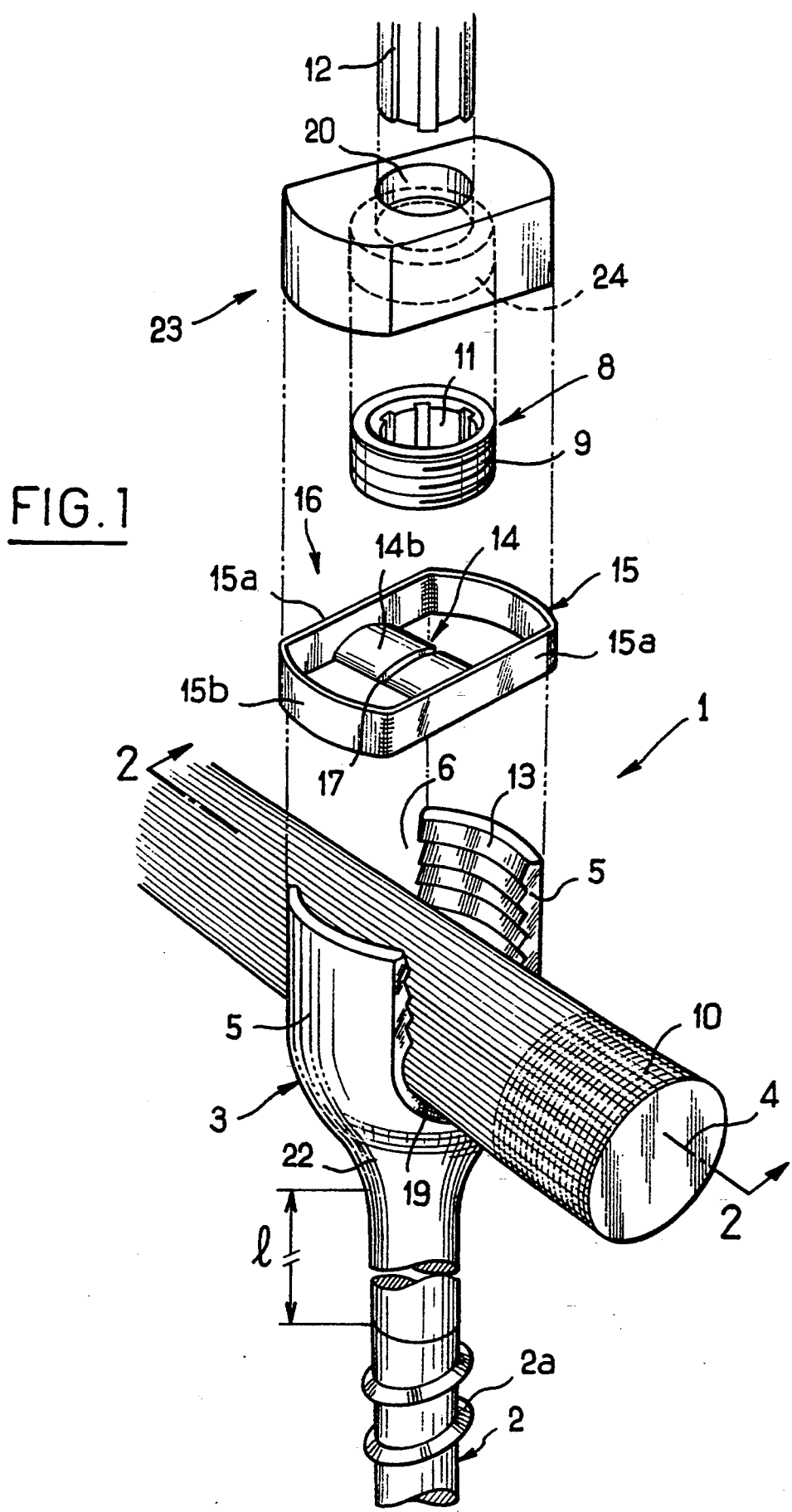
FIG. 1 is an exploded perspective view of an embodiment of the implant according to the invention to a very large scale.

The implant 1 shown in the drawings is intended for an osteosynthesis device (not shown), in particular for the backbone. It comprises a part 2 for anchorage in the bone, here formed by a screwthreaded stem, which may be replaced by a hook.

The implant further comprises a body 3 for fixing to a rod 4 having asperities, for example a knurled rod or a rod having diamond points. The body 3 comprises two lateral branches 5 defining a passageway 6 opening onto a rear part of the body 3 and open on each side of the latter for receiving the rod 4. The body 3 consequently has a U-shaped section in a transverse plane of the passageway 6.

The implant also comprises a plug 8 provided with a screw thread 9 and in which is machined a suitably shaped cavity 11 for receiving a corresponding tool 12 for screwing the plug 8 in tappings 13 formed on the inner sides of the two lateral branches 5.

The implant 1 comprises a connection element between the plug 8 and the rod 4, constituted by a strip 14 fixed to a ring 15 for positioning the strip 14 with respect to the branches 5, the pellet 16 formed by the strip 14 and the ring 15 being made in one piece by press-forming and blanking a sheet of metal, which permits considerable savings in manufacturing costs.

The strip 14 extends from one end to the other of the passageway 6, its width being substantially less than the width of the entrance of the passageway.

The strip 14 defines adjacent to the rod 4 a concave surface 14a adapted to be applied against the surface of the rod 4, and a corresponding convex surface 14b adjacent to the plug 8. The whole of the strip 14 thus forms a portion of a cylinder imparting thereto the general shape of a half-round tile whose radius of curvature substantially corresponds to the radius of curvature of the surface of the rod 4. Preferably, as shown, the strip 14 is cut substantially in the middle thereof and is thus constituted by two semi-strips 14c separated by a slot 17 substantially perpendicular to the axis of the rod 4. There are advantageously provided in the concave surfaces 14a of the semi-strips 14c negative impressions 18 (FIG. 3) of the asperities of the rod 4, for example diamond points.

The ring 15 of the pellet 16 is so dimensioned as to surround the branches 5 when it is placed in position on the body 3 by insertion of the branches 5 in the gaps provided between the longitudinal edges of the strip 14 and the inner side of the ring 15. The latter comprises two parallel rectilinear portions 15a defining flat surfaces perpendicular to the axis of the rod 4 and connected to opposite ends of the semi-strips 14c, and two part-circular portions 15b interconnecting the opposite ends of the flat surfaces 15a. The part-circular portions 15b have a radius of curvature corresponding to the radius of curvature of the outer surface of the branches 5 against which they are applied when the pellet 16 is mounted on the body 3.

The passageway 6 has an inner end 19 in the central zone of which is formed a recess 21 which extends in the same direction as the axis of the rod 4. The stem 2 is provided with a screw thread 2a whose end adjacent to the body 3 is separated from the body by a smooth zone 22 whose length l, for a given total length of the screw, is larger than the usual length of the smooth zones of conventional screws. Indeed, this length l is preferably at least substantially equal to the length of the branches 5 of the body 3.

A block 23 of flexible material, preferably a suitable plastics material, is advantageously employed for placing in position the elements clamping the rod 4 in the body 3, i.e. the pellet 16 and the plug 8. This block has an outer shape similar to that of the ring 15 and is so dimensioned that, after compression, one of its surfaces can engage the interior of the ring 15, which is in this way temporarily connected to the block 23. Provided in the latter is a cavity 24 for receiving the plug 8, this cavity 24 therefore opening onto the surface of the block 23 facing toward the pellet 16 and the rod 4 when the various elements are positioned for their assembly. The cavity 24 is extended on the side of the block 23 remote from the pellet 16 by a central bore 20 allowing the insertion of the end of the tool 12 which has a suitable cross-sectional shape for fitting in the cross-sectional shape of the opening 11 of the plug 8 to permit screwing the latter. The cavity 24 is so dimensioned that the plug 8 partly projects from the block 23 when it is placed in this cavity so that the screw thread on this projecting end portion can threadedly engage the tappings 13.

The clamping elements 8 and 16 are placed in position by the surgeon by means of the flexible block 23 in the following manner:

First of all the plug 8 is inserted in the cavity 24 and then the surface of the block 23 from which the plug partly projects is compressed so as to be capable of insertion in the ring 15 whose contour corresponds to that of the block 23 to which it is in this way temporarily connected by an elastic compression of the block. By means of the tool 12 engaged in the bore 20 and the cavity 24, the surgeon moves these three elements 23, 8, 16 toward the body 3 along the branches 5 of which he slides the ring 15. The strip 14 is positioned in the passageway 6 close to the cylindrical surface of the rod 4.

Rotating the tool 12 drives the plug 8 in rotation and gradually screws it between the tappings 13. The displacement of the plug 8 displaces the pellet 16 whose semi-strips 14c and the flat surfaces 15a come to be firmly applied against the rod 4. At the end of the screwing of the plug 8, the block 23 is completely detached from the pellet 16 and plug 8 and can be discarded.

In addition to those already mentioned, the implant according to the invention has the following advantages:

The increase in the bending inertia of the strip 14, achieved by its curved shape complementary to that of the surface of the rod 4, avoids a local deformation of this strip between the plug 8 and the rod 4. This improvement very substantially reduces the required specific pressure on the rod 4 and achieves an improved centering of the strip 14 on the rod, which in turn permits a positioning of the impressions 18 in the strip 14 on the asperities (diamond points) of the rod 4. There is correspondingly avoided a tendency to bruise the zones of contact between the plug and the strip and between the latter and the rod. The resistance to alternating bending of the rod in the body is therefore increased in the same way as the resistance to fatigue of the implant.

The negative impressions 18 very substantially improve the resistance to sliding between the components of the assembly and permit reducing the clamping force required to ensure the suitable characteristics of the implant.

The fact that the strip 14 is made in two semi-strips 14c results in an improved contact in the two zones of the strip 14 engaging the rod 4, which is particularly advantageous if the latter is curved or inclined in the passageway 6, the surface of contact being in this way increased with corresponding increase in the resistance to pulling away.

The geometry of the ring 15 reduces the width of the implant 1 in the direction in which the rod 4 extends, owing to the design of the rectilinear portions 15a perpendicular to the rod 4, which makes for short assemblies, in particular in the lumbar region of the backbone where the radii of curvature are very large and bring the bodies of the screw closer together.

The two rectilinear portions 15a of the ring 15 are close to the screw thread 9 of the plug 8. In this way it is possible, by means of a known tool available to the surgeon, to deform the two flat surfaces 15a and clamp the plug 8 by deforming its screw threads, which in this way resists the unscrewing of the plug and avoids any risk of an untimely disassembly of this plug after the implant has been placed in the patient. The design of the rectilinear portions 15a therefore constitutes an important technical advantage.

The ring 15 maintains the two branches 5 around the plug 8 from which they cannot move away after screwing. The contour of the ring 15 marries up in the best possible manner with the body 3 and therefore provides an improved resistance of a pulling away of the plug 8.

The recess 21 provided in the inner end 19 of the passageway 6 provides a support for the rod 4 at two points or two zones 21a and consequently an improved stability of the rod as concerns bending, above all in the practically general case of a curved rod.

Figure 4:
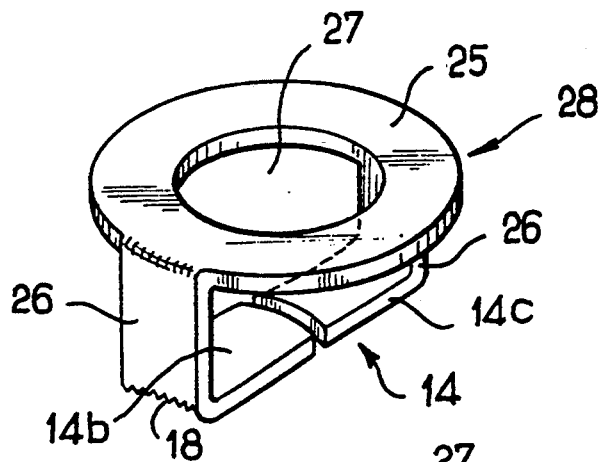
FIG. 4 is a perspective view to an enlarged scale of a second embodiment of the pellet of the implant according to the invention, formed by the strip and the means for positioning the latter.
Figure 6:
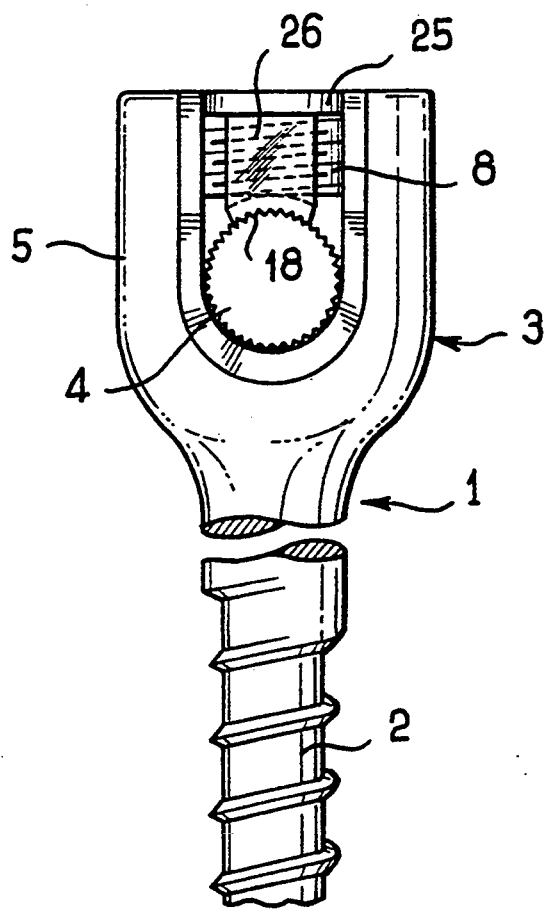
FIG. 6 is an elevational view to an enlarged scale on the axis of the rod, of the implant provided with the retaining pellet of FIG. 4.

In the second embodiment of the invention illustrated in FIGS. 4 and 6, the means for positioning the strip 14 divided into two semi-strips 14c separated by the slot 17, is a ring 25 connected to two curved semi-strips 14c by two side walls 26. The latter are diametrically opposed and make substantially a right angle with the ring 25 and are each extended by a semi-strip 14c also making substantially a right angle with the associated side wall 26. The unit comprising the elements 14c, 25 and 26 constitutes a pellet 28 made in a single piece from a suitably press-formed and blanked strip or plate.

The outside diameter of the ring 25 is equal to that of the plug 8 minus the height of its screw thread. The diameter of the opening 27 of the ring 25 is at least equal to the diameter of the bore 11 in the plug 8.

The plug 8 is inserted laterally between the side walls 26 on one hand and between the strip 14 and the ring 25 on the other. The surgeon then places in position the parts 28 and 8 in the passageway 6 and then screws the plug 8 by means of a tool extending through the opening 27 in the ring 25.

Figure 3:
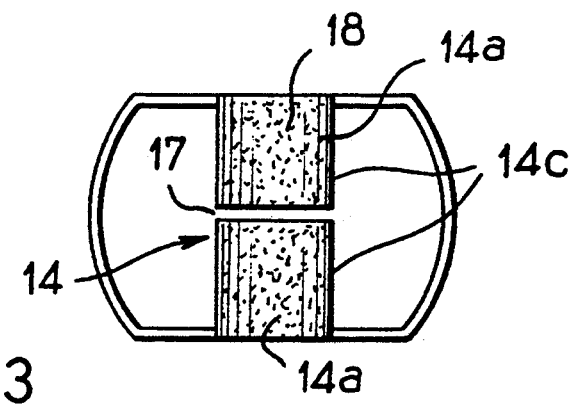
FIG. 3 is a top plan view of a pellet shown in FIGS. 1 and 2 constituted by the strip and the ring for fixing the strip relative to the branches of the body.
Figure 2:
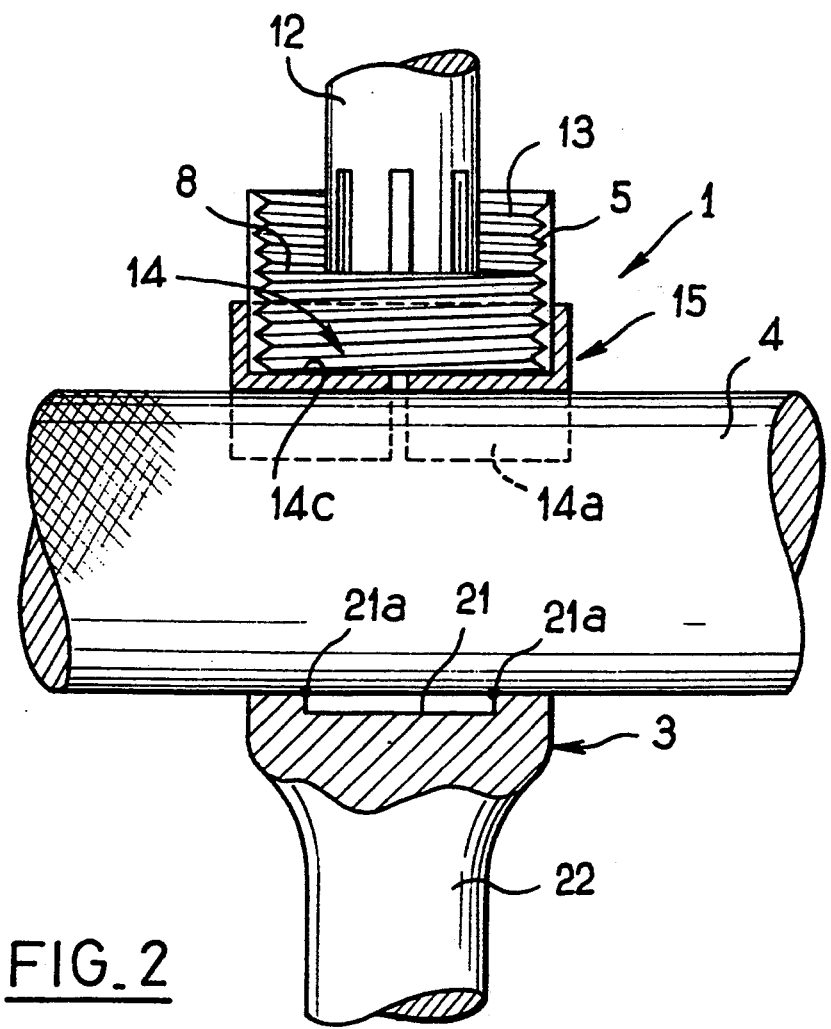
FIG. 2 is a semi-sectional semi-elevational view of the implant taken on line 2—2 of FIG. 1, the various component parts of which are assembled, and of a tool for assembling these parts.

The advantages of this embodiment are the same as those of FIGS. 1 to 3 (apart from those specific to the ring 15) and, in addition, in this second embodiment, the implant has a reduced transverse overall size owing to the elimination of the thickness of the ring 15 outside the branches 5.

Further, the side walls 26 may be clamped by a punching thereof against the plug 8 by means of a suitable known punching tool so that the plug is locked in position against any risk of an accidental unscrewing after the implant has been placed in position.

Figure 5:
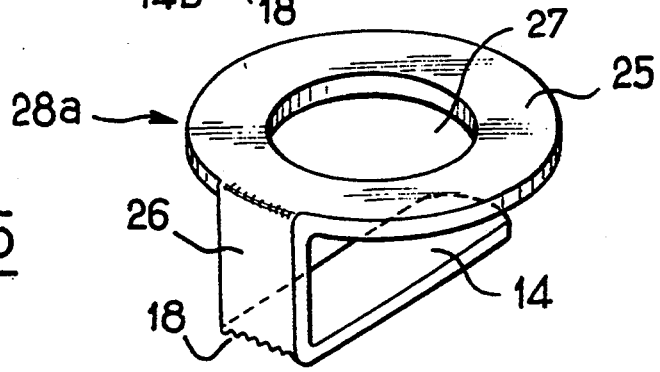
FIG. 5 is a view similar to FIG. 4 of an alternative embodiment of the pellet.

The alternative embodiment of the pellet 28a shown in FIG. 5 differs from the pellet 28 of FIG. 4 in that it has only a single side wall 26 and a single strip 14 which extends in a direction substantially parallel to the plane of the ring 25.

In the two embodiments, the pellets 28 and 28a have their bent strips 14 advantageously provided with impressions 18 as shown in FIG. 3, which locks the rod 4 in position upon the screwing of the plug 8.

The scope of the invention is not intended to be limited to the described embodiments and encompasses various alternative arrangements. Thus the contour of the ring 15 with two flat portions 15a and two part-circular portions 15b is not obligatory and the strip 14 is not necessarily divided into two semi-strips 14c (FIGS. 1 to 3). The convex surface 14b of the strip 14 could be replaced by a planar surface.

What is claimed is:

1. An implant for an osteosynthesis device for engaging an elongated rod to a bone, comprising:
   a bone anchoring element including;
      a bone engaging portion configured to engage the bone; and
      a rod securing portion including a body member having two branches defining a channel therebetween adapted for receiving the elongated rod therein, said body member being open at a rear portion thereof and said branches having threaded inner surfaces facing said channel and extending from said rear portion;
   a plug threaded for engagement with said threaded inner surfaces of said branches to close said open rear portion of said body member and secure the elongated rod therein when the rod is disposed within said channel; and
   a connection element including a strip configured to be received within said channel and positioning means connected to said strip for positioning said strip relative to said branches, said strip further having a surface facing said plug when said plug is in threaded engagement with said inner surfaces and an opposite surface facing the elongated rod when the rod is within said channel,
   whereby when said plug is threaded into said channel said plug bears on said strip of said connection element which bears on the elongated rod to clamp the rod within said channel.

2. The implant according to claim 1, in which the elongated rod is cylindrical and wherein said opposite surface of said strip defines a concave surface toward the cylindrical rod.

3. The implant according to claim 1, wherein said opposite surface defines a plurality of depressions thereon for engaging the elongated rod.

4. The implant according to claim 1, wherein said surface facing said plug defines a convex surface toward said plug.

5. The implant according to claim 4, in which the elongated rod is cylindrical and wherein said opposite surface which is of said strip defines a concave surface toward the cylindrical rod when the rod is within the channel.

6. The implant according to claim 1, wherein:
   said branches have outer surfaces opposite said inner surfaces; and
   said positioning means includes a ring surrounding said outer surfaces of said branches.

7. The implant according to claim 6, wherein:
   said outer surfaces of said branches are curved; and
   said ring of said positioning means includes a pair of opposite rectilinear portions connected by a pair of semi-circular portions, the radius of curvature of said semi-circular portions being substantially complementary to said curved outer surfaces of said branches.

8. The implant according to claim 6, wherein said strip includes two strip portions, each connected at one end thereof to said ring and defining a slot between opposite ends of said strip portions.

9. The implant according to claim 1, wherein said strip includes two strip portions separated by a slot.

10. The implant according to claim 1, wherein said bone engaging portion of said bone anchoring element includes a threaded shank portion attached to said body member by a smooth shank portion, said smooth shank portion having a length and said branches having a length that are substantially equal to each other.

11. The implant of claim 1, wherein said positioning means includes:
   a ring dimensioned to be received through said open rear portion of said body member and between said inner surfaces of said branches; and
   a means for connecting said ring to said strip.

12. The implant of claim 11, wherein said ring is an annular ring defining an opening therethrough.

13. The implant of claim 12, wherein said ring is connected to one end of said strip by a side wall so that said ring and said strip are disposed apart a distance sufficient to receive said threaded plug therebetween.

14. The implant of claim 12, wherein:
   said plug includes a tool opening defined therein to accept a driving tool; and
   said opening in said annular ring is sized to receive the driving tool therethrough for access to said tool opening.

* * * * *